United States Patent
Silva et al.

(10) Patent No.: US 11,612,121 B2
(45) Date of Patent: Mar. 28, 2023

(54) METHODS OF PRODUCING SUGAR CANE TRANSPLANT UNITS

(71) Applicant: Syngenta Participations AG, Basel (CH)

(72) Inventors: Adilson Donizeti Correa Da Silva, Sao Paulo (BR); Luis Batista, Sao Paulo (BR); Luiz Vidal, Sao Paulo (BR)

(73) Assignee: Syngenta Participations AG, Basel (CH)

( * ) Notice: Subject to any disclaimer, the term of this patent is extended or adjusted under 35 U.S.C. 154(b) by 164 days.

(21) Appl. No.: 16/093,955

(22) PCT Filed: Apr. 10, 2017

(86) PCT No.: PCT/US2017/026747
§ 371 (c)(1),
(2) Date: Oct. 15, 2018

(87) PCT Pub. No.: WO2017/180490
PCT Pub. Date: Oct. 19, 2017

(65) Prior Publication Data
US 2020/0323155 A1    Oct. 15, 2020

(51) Int. Cl.
| | |
|---|---|
| *A01G 22/55* | (2018.01) |
| *A01H 4/00* | (2006.01) |
| *A01D 45/10* | (2006.01) |
| *A01G 7/06* | (2006.01) |
| *A01N 43/38* | (2006.01) |
| *A01N 59/16* | (2006.01) |
| *A01G 2/10* | (2018.01) |
| *A01C 14/00* | (2006.01) |
| *A01N 59/00* | (2006.01) |
| *A01B 79/02* | (2006.01) |
| *A01N 51/00* | (2006.01) |
| *A01N 25/00* | (2006.01) |

(52) U.S. Cl.
CPC .............. *A01H 4/00* (2013.01); *A01B 79/02* (2013.01); *A01C 14/00* (2013.01); *A01D 45/10* (2013.01); *A01G 2/10* (2018.02); *A01G 7/06* (2013.01); *A01G 22/55* (2018.02); *A01H 4/005* (2013.01); *A01H 4/008* (2013.01); *A01N 25/00* (2013.01); *A01N 43/38* (2013.01); *A01N 51/00* (2013.01); *A01N 59/00* (2013.01); *A01N 59/16* (2013.01); *A01N 2300/00* (2013.01)

(58) Field of Classification Search
CPC .......... A01B 79/02; A01C 14/00; A01G 1/00; A01G 2/10; A01G 22/55; A01G 7/06; A01H 4/00; A01H 4/005; A01H 4/06; A01N 59/16; A01N 43/78; A01N 43/38; A01N 51/00; A01N 43/90; A01N 47/40; A01N 47/24; A01N 47/02; A01N 43/56; A01N 2300/00; A01N 25/00; C12N 15/8245
USPC .......................... 800/295, 298, 320; 504/100
See application file for complete search history.

(56) References Cited

U.S. PATENT DOCUMENTS

| | | | |
|---|---|---|---|
| 4,204,491 A | 5/1980 | Quick | |
| 6,521,452 B1 * | 2/2003 | Abdelrahman | A01H 4/005 435/410 |
| 6,712,013 B2 | 3/2004 | Gould et al. | |
| 8,952,219 B2 | 2/2015 | De Lucca et al. | |
| 2005/0016145 A1 | 1/2005 | Huff, Jr. | |
| 2010/0263095 A1 * | 10/2010 | Aramaki | A01C 11/00 800/320 |
| 2011/0008463 A1 * | 1/2011 | Bosselaers | A01N 43/40 424/618 |

FOREIGN PATENT DOCUMENTS

| | | | | |
|---|---|---|---|---|
| CN | 100421541 | | 10/2008 | |
| CN | 100421541 C | * | 10/2008 | |
| WO | WO-2011019984 A3 | * | 6/2011 | ............. A01G 20/00 |
| WO | WO-2015138277 A1 | * | 9/2015 | ............... A01N 3/00 |

OTHER PUBLICATIONS

Bureau of sugar experiment stations Queensland, Australia, Literature Review of Methods of Improving the Germination of Sugarcane, by Barry J Croft PR00002, Jul. 2000, downloaded from https://elibrary.sugarresearch.com.au/bitstream/handle/11079/922/ BSS208%20Final%20report.pdf?sequence=1&isAllowed=y (Year: 2000).*

International Search Report cited in International Application No. PCT/US2017/026747 filed Apr. 10, 2017, dated Jun. 28, 2017.

* cited by examiner

*Primary Examiner* — Anne Marie Grunberg
(74) *Attorney, Agent, or Firm* — BakerHostetler; Toni-Junell Herbert

(57) ABSTRACT

Methods of producing sugar cane transplant units that includes planting a sugar cane propagation material in a planting container that has a volume of 10 to 200 cubic centimeters; growing the sugar plant to an age of at least 4 months; harvesting the stalks of the sugar cane plant when the stalks have a length of 10 to 50 centimeters; cutting the harvested stalks into stalk segments, wherein the stalk segments are cut to a length of 1 to 5 centimeters; and planting one or more of the stalk segments into a planting container that has a volume from 10 to 200 cubic centimeters.

20 Claims, 4 Drawing Sheets

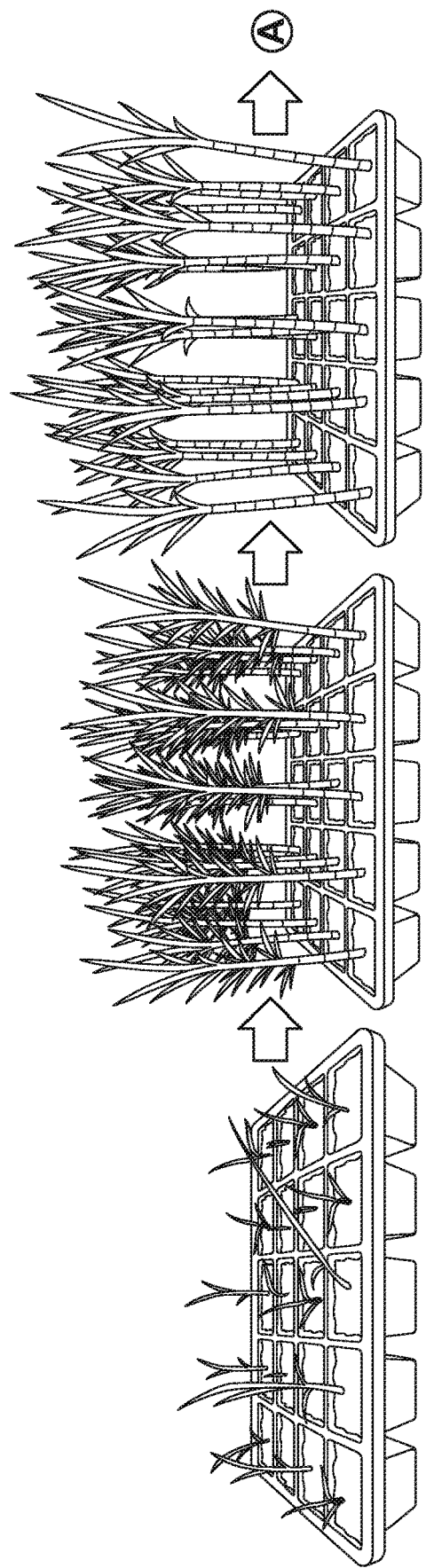

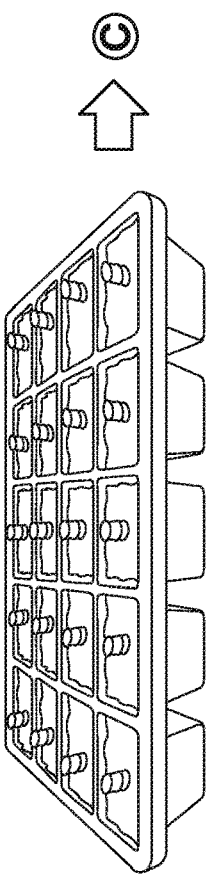
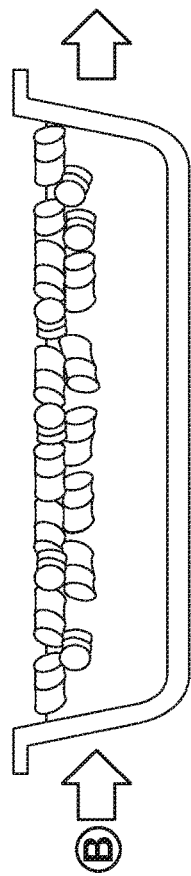

500

METHODS OF PRODUCING SUGAR CANE TRANSPLANT UNITS

RELATED APPLICATION INFORMATION

This application is a 371 of International Application No. PCT/US02017/026747, filed Apr. 10, 2017, which claims priority to U.S. Application No. 62/322,894, filed Apr. 15, 2016, the contents of which are incorporated herein by reference herein.

DRAWINGS

FIGS. 1-4 is a schematic process diagram in accordance with the present technology.

FIG. 1(a) is a schematic representation of a sugar cane plantlet in accordance with the present technology.

FIG. 1(b) is a schematic representation of a sugar cane plant in accordance with the present technology.

FIG. 1(c) is a schematic representation of a sugar cane plant which has been partially dehusked in accordance with the present technology.

FIG. 3(a) is a schematic representation of sugar cane stalk segment immersed in a hot water treatment bath in accordance with the present technology.

FIG. 3(b) is a schematic representation of a sugar cane stem section placed in a multi-cell tray in accordance with the present technology.

DESCRIPTION

Figure 2B:
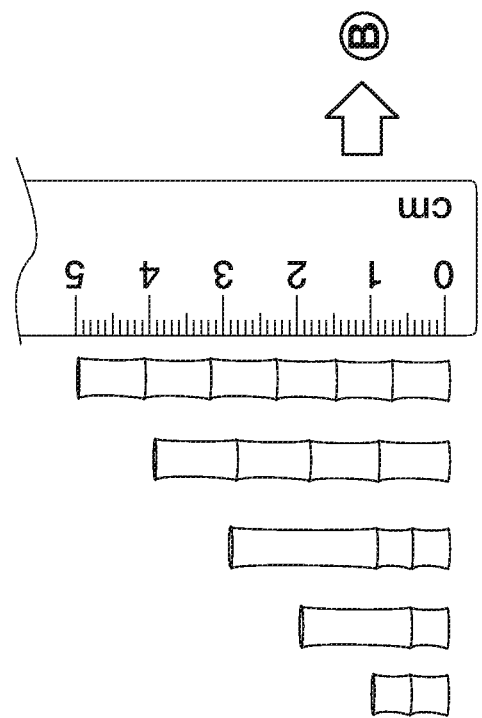
FIG. 2(b) is a schematic representation of a sugar cane stalk segment(s) in accordance with the present technology.
Figure 2A:
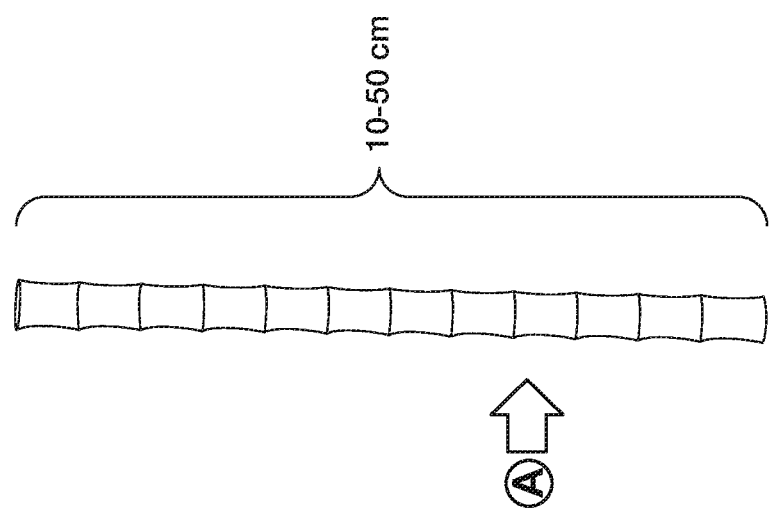
FIG. 2(a) is a schematic representation of a harvested sugar cane stalk in accordance with the present technology.
Figure 4B:
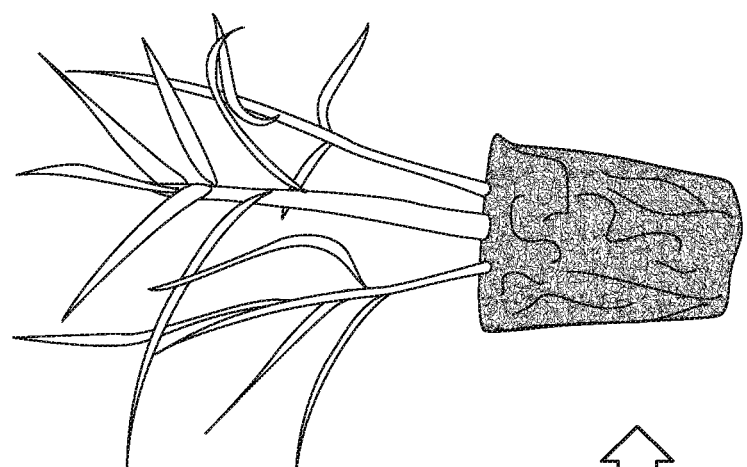
FIG. 4(b) is a schematic representation of a sugar cane transplant unit in accordance with the present technology.
Figure 4A:
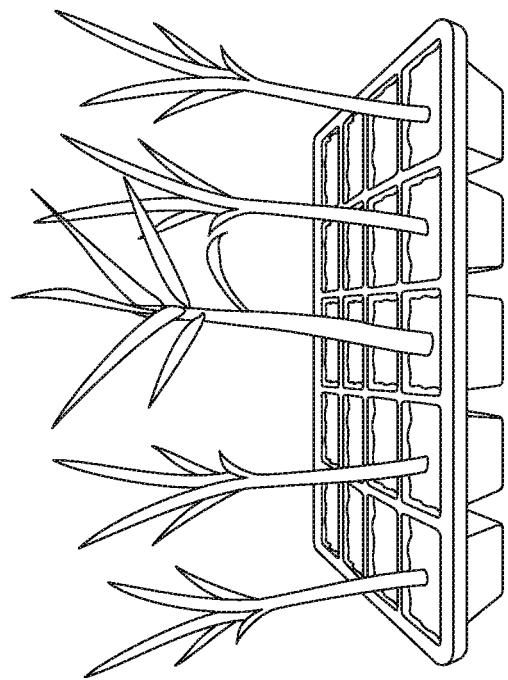
FIG. 4(a) is a schematic representation of a sugar cane transplant units in a multi-cell tray in accordance with the present technology.

The present application relates generally to the field of plant propagation. In particular, the present invention relates to methods of growing sugar cane plants for transplanting.

The term "stalk" as used herein is the portion the sugar cane plant which includes nodes and internodes.

The term "node" is the area around the sugar cane bud from the leaf scar to the growth ring and is the part of the stalk from which a leaf, branch, or aerial root grows.

The term "internode" is the part of the stalk between two nodes.

The term "plant propagation material" or "propagation material" are plants and parts thereof that are intended for plant cultivation or propagation.

The present invention is directed to methods of producing sugar cane plants for transplanting, and in particular, for producing a sugar cane transplant unit. In agriculture, transplanting is the technique of moving a plant from one location to another. Generally, transplanting takes the form of starting a plant from plant propagation material under controlled conditions, such as a greenhouse or nursery, then replanting in another growing location, commonly a field.

Transplant productions systems generally include containerized and non-containerized systems. Containerized transplants allow separately grown plants to be transplanted with the roots and soil intact. Containers may include, but are not limited to, biodegradable pots (e.g., peat pots—a pot made of compressed peat), soil blocks (compressed blocks of soil), multiple-cell containers, and plug trays. Such container options are well known in the field of agricultural transplanting.

As used herein, the terms "first" and "second" as they relate to planting containers are used for the purposes of antecedent basis only and not to imply order-of-use or a required quantity of a planting container. It is envisioned that that the planting containers themselves may be identical to each other or the same container used at a different step in the process, however, the containers need not be identical or the same container.

In one embodiment of the invention, the invention includes a method of producing a sugar cane planting unit. This embodiment provides for a method comprising:

a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;

b. growing the sugar plant to an age of at least 4 months;

c. harvesting the stalks of the sugar cane plant when the stalks have a length of 10 to 50 centimeters;

d. cutting the harvested stalks into stalk segments, wherein the stalk segments are cut to a length of 1 to 5 centimeters;

e. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:

a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;

b. growing the sugar plant to an age of 4 to 24 months;

c. harvesting the stalks of the sugar cane plant when the stalks have a length of 10 to 50 centimeters;

d. cutting the harvested stalks into stalk segments, wherein the stalk segments are cut to a length of 1 to 5 centimeters;

e. treating the stalk segments with water and a plant growth regulator, wherein the water temperature is 45° C. to 55° C.; and f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:

a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;

b. growing the sugar plant to an age of 4 to 18 months, wherein the sugar cane plant has 1 to 4 stalks;

c. harvesting the stalks of the sugar cane plant when the stalks have a length of 10 to 50 centimeters;

d. cutting the harvested stalks into stalk segments, wherein the stalk segments are cut to a length of 1 to 5 centimeters;
e. treating the stalk segments with water and a crop protection chemical, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant when the stalks have a length of 10 to 50 centimeters;
d. cutting the harvested stalks into stalk segments, wherein the stalk segments are cut to a length of 1 to 5 centimeters;
e. treating the stalk segments with water and a crop protection chemical, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant when the stalks have a length of 10 to 50 centimeters;
d. cutting the harvested stalks into stalk segments, wherein the stalk segments are cut to a length of 1 to 5 centimeters;
e. treating the stalk segments with water and a plant growth regulator, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant when stalks have a length of 10 to 50 centimeters;
d. cutting the harvested stalks into stalk segments, wherein the stalk segments are cut to a length of 1 to 5 centimeters;
e. treating the stalk segments with water and a plant growth regulator, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant when the stalks have a length of 10 to 50 centimeters;
d. cutting the harvested stalks into stalk segments, wherein the stalk segments are cut to a length of 1 to 5 centimeters;
e. treating the stalk segments with water and a one or more plant growth regulators, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant when the stalks have a length of 10 to 50 centimeters;
d. cutting the harvested stalks into stalk segments, wherein the stalk segments are cut to a length of 1 to 5 centimeters;

e. treating the stalk segments with water and one or more plant growth regulators and one or more fungicides, wherein the water temperature is 45° C. to 55° C.; and
f. planting one or more of the stalk segments into a second planting container comprising a planting medium to form a planting unit, wherein said second planting container has a volume from 10 to 200 cubic centimeters.

In one embodiment of the invention, the invention includes a method of producing a sugar cane planting unit. This embodiment provides for a method comprising:
a. planting a sugar cane propagation material in a first planting container to produce a sugar cane plant, wherein the sugar cane propagation material is a plant produced from tissue culture or a sugar cane billet, and wherein the first planting container has a volume of 10 to 200 cubic centimeters;
b. growing the sugar plant to an age of 4 to 18 months, wherein the sugar cane plant has 1 to 4 stalks and at least one stalk has a linear node density of at least 1 node per 3 centimeters of stalk;
c. harvesting the stalks of the sugar cane plant, wherein the stalks have a length of 10 to 50 centimeters;
d. cutting the harvested stalks into stalk segments, wherein the stalk segments are cut to a length of 1 to 5 centimeters;
e. treating the stalk segments with a solution of water, indole-3-butyric acid, and thiabendazole, wherein the water temperature is 45° C. to 55° C.; and
f. planting one or more of the stalk segments into a second planting container comprising a planting medium to form a planting unit, wherein said second planting container has a volume from 10 to 200 cubic centimeters.

Planting and Growing

The present technology provides for planting and growing sugar plants. In one embodiment, the present technology includes two planting steps, a first planting to grow a sugar cane plant, and a second planting to create a planting unit.

The first planting step includes planting a sugar cane propagation material into a planting container. The planting container is generally of volume between 10 and 200 cubic centimeters. In another embodiment, the first planting container is between 10 and 100 cubic centimeters. In another embodiment, the first planting container is between 10 and 50 cubic centimeters. In another embodiment, the first planting container is between 20 and 40 cubic centimeters. In another embodiment, the first planting container is between 25 and 35 cubic centimeters. In a preferred embodiment, the container is a multi-cell container which has 25 or more cells. In another preferred embodiment, the container is a multi-cell container which has 50 or more cells.

The plant propagation material for the first planting step is generally selected from a sugar cane plant produced from tissue culture or a sugar cane billet. Such sugar cane propagation material is well-known by those of skill in the art. In one preferred embodiment, the sugar cane plant propagation material is a billet with a single node. In another preferred embodiment, the sugar cane plant propagation material is a plant produced from tissue culture. A plant produced from tissue culture is commonly produced through micro-propagation. Micro-propagation generally includes steps of establishment, multiplication, rooting, and transfer from culture.

The growing of sugar cane plant generally occurs in the planting container which the sugar can propagation material was planted or the plantlet could be transferred another similar sized container in the volume range of between 10 and 200 cubic centimeters. The restricted volume of the growth container(s) allows for control over the size of the sugar cane plant. The restricted volume generally results in a sugar cane plant that appears as miniature sugar cane plant as compared to a sugar cane plant without growth restriction.

In one embodiment the sugar cane plants are allowed to grow in the container for at least 4 months. In another embodiment the sugar cane plants are grown to age of between 4 to 24 months. In another embodiment the sugar cane plants are grown to age of between 4 to 18 months.

The second planting step includes planting a sugar cane propagation material into a planting container to form a transplant unit. The planting container is generally of volume between 10 and 200 cubic centimeters. In another embodiment, the second planting container is between 10 and 100 cubic centimeters. In another embodiment, the second planting container is between 50 and 200 cubic centimeters. In another embodiment, the second planting container is between 50 and 150 cubic centimeters. In another embodiment, the second planting container is between 75 and 125 cubic centimeters. In another embodiment, the second planting container is between 95 and 105 cubic centimeters. In a preferred embodiment, the container is a multi-cell container which has 25 or more cells.

The term "planting medium" or "growing medium" is the material used in a container to grow a plant. Planting mediums are well known in the art and the composition of such medium are commonly adapted to the grower's needs and local environment. There are many different ingredients that can be used to make a growing medium; different parts of the world have developed media based on local availability of various raw materials. Such materials may include both inorganic materials (e.g. rockwool, perlite) and organic materials (such as peat, bark). Growing media are often formulated from a blend of different raw materials in order to achieve the correct balance of air and water holding capacity for the plants to be grown. The requirements and/or functionality of a growing medium general provide anchorage for the plant; provide adequate air spaces for root respiration; hold sufficient available water; hold sufficient available nutrients; is free of plant pathogens, pests and weeds; and is safe when handled by people. Growing media is generally physically and chemically stable from the time of production until the time of use. The bulk density of the ingredients used may also important because this affects transport costs, a major part of the total cost of production and delivery to the end customer.

The growing media may also be treated with crop protection chemicals, for example, with fungicides, insecticides and nematicides in order to provide plant protection against diseases, insects, fungus and nematodes.

Harvesting and Dehusking

Harvesting of the stalks can be performed by any known method and generally includes at least separating the stalk from the root system. The leaves of the sugar cane plant may also be removed, a technique called dehusking.

The harvesting step of the present invention occurs after the plants have reached an age of between 4 and 18 months and have reached a stalk height of 10 to 50 centimeters.

At the time of harvest, the stalk or stalks preferably have an average linear node density of at least 1 node per 3 centimeters of stalk.

Separation of the stalk from the root system is generally performed by cutting via shearing (e.g., with a knife) or sawing, which can be performed either manually or mechanically.

In one embodiment of the present technology, the harvesting step is performed by passing a multi-cell planting container through a fixed height cutting device to separate the stalks from the root systems.

In another embodiment of the present technology, the harvesting step is performed manually using a hand-held cutting device.

Cutting

Cutting the harvested stalks into stalk segments can be performed by any known method. Such cutting can be performed manually by hand, or with the use of machine.

The cutting of stalks into stalk segments of the preset technology is directed to cutting the stalks into stalk segment sizes of 1 to 5 cm in length and where the stalk segment contains at least one node.

Treating

The treating step includes, but is not limited to, a hot water treatment, application of plant nutrients, application of pesticides, application of plant growth regulators, or application of other suitable agricultural chemistries.

In one embodiment, the treating step includes a hot water treatment that contains a concentration of one or more plant growth regulators and one or more fungicides, insecticides, safeners, and/or nematicides. In this embodiment, the treatment step is one or more plant growth regulators and one or more fungicides are added to a hot water bath and the stalk segment are immersed in the bath for a given time. The concentration of a given plant growth regulator, fungicide, insecticide, safener, or nematicide are readily determined by those of skill in the art. Hot water treatments are known, particularly in horticulture, to kill bacterial disease causing organism on or within plant propagation materials. Known hot water treatment temperatures are generally 45° C. to 50° C. and require a soak time of 15 to 30 minutes. In sugar cane, hot water treatment is commonly suggested to control ratoon stunting disease (RSD) by immersing sugar cane billets in 50° C. for 2 hours. In the present invention, however, the hot water treatment step can be performed in 1 to 10 minutes, and preferably in 2 to 3 minutes.

When plant growth regulators are included in the hot water treatment, a concentration will be determined. A person of skill in art can determine and apply an appropriate concentration based on the selection of plant growth regulator applied. As a general guide, the following concentrations are examples:

TABLE 1

| | Plant Growth Regulator Concentrations (grams/liter) | |
|---|---|---|
| Range | Lower Limit | Upper Limit |
| 1 | 0.01 | 100 |
| 2 | 0.025 | 90 |
| 3 | 0.05 | 80 |
| 4 | 0.075 | 70 |
| 5 | 0.09 | 60 |
| 6 | 0.1 | 50 |
| 7 | 0.1 | 40 |
| 8 | 0.25 | 20 |
| 9 | 0.5 | 10 |
| 10 | 0.5 | 5 |

Plant growth regulators are any substances or mixtures of substances intended to alter the germination, growth, maturation, or development of plants or their produce. Plant growth regulators may be classified into subcategories including, but not limited to antiauxins (clofibric acid, 2,3,5-tri-iodobenzoic acid), auxins (4-CPA, 2,4-D, 2,4-DB, 2,4-DEP, dichlorprop, fenoprop, IAA, IBA, naphthaleneacetamide, α-naphthaleneacetic acid, 1-naphthol, naphthoxyacetic acid, potassium naphthenate, sodium naphthenate, 2,4,5-T), cytokinins (2iP, benzyladenine, kinetin, zeatin), defoliants (calcium cyanamide, dimethipin, endothal, ethephon, merphos, metoxuron, pentachlorophenol, thidiazuron, tribufos), ethylene inhibitors (aviglycine, 1-methylcyclopropene), ethylene releasers (ACC, etacelasil, ethephon, glyoxime), gibberellins (gibberellic acid, gibberellins, including non-cyclopropene compounds that show gibberellin-like activity, such as, for example, helminthosporic acid, phaseolic acid, kaurenoic acid, and steviol), growth inhibitors (abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham 2,3,5-tri-iodobenzoic acid), morphactins (chlorfluren, chlorflurenol, dichlorflurenol, flurenol), growth retardants/modifiers (chlormequat, daminozide, flurprimidol, mefluidide, paclobutrazol, cyproconazole, tetcyclacis, uniconazole, ancymidol, trinexapac-ethyl, and progexadione-CA), growth stimulators (brassinolide, forchlorfenuron, hymexazol, 2-amino-6-oxypurine derivatives, as described below, indolinone derivates, as described below, 3,4-disubstituted maleimide derivatives, as described below, and fused azepinone derivatives, as described below). The term additionally includes other active ingredients such as benzofluor, buminafos, carvone, ciobutide, clofencet, cloxyfonac, cyclanilide, cycloheximide, epocholeone, ethychlozate, ethylene, fenridazon, heptopargil, holosulf, inabenfide, karetazan, lead arsenate, methasulfocarb, prohexadione, pydanon, sintofen, triapenthenol, and trinexapac. Preferred plant growth regulators include growth retardants, the class of gibberellins, including gibberellic acid, growth inhibitors, and growth stimulators.

In another embodiment, the plant growth regulator is a hormone selected from cytokinins and auxins. Preferred cytokinins may be selected from the group consisting of kinetin, zeatin, 6-benzylaminopurine, diphenyl urea, and thidiazuron. Preferred auxins may be selected from the group consisting of indole-3-actetic acid (IAA), 4-chloroindole-3-acetic acid (4-CI-IAA), 2-phenylacetic acid (PAA), and indole-3-butyric acid (IBA).

While the preferred embodiment of applying agricultural chemicals such as plant growth regulators and fungicides is a hot water treatment, such description is not intended to, and does not, limit the scope the present invention to such treatment type. Other treatment method are intended to be encompasses in such treatment step. These treating methods include, by way of example and not by limitation, dressing, spraying, coating and the already described soaking methods. Conventional treating techniques and machines can be used, such as fluidized beds, roller mills, rotostatic seed treaters, drum coaters, and spouted beds. The techniques of propagation material treatment applications are well known to those skilled in the art, and they may be used readily in the context of the present invention. Needless to say, the method of application of the inventive compositions to the propagation material may be varied and the invention is intended to include any technique that is to be used.

Crop Protection Chemicals

Additional crop protection chemicals may be applied to propagation material, to the planting mediums of either of the planting steps describe herein, or to the plant itself.

Crop protection chemicals are known in the art and include, for example and among others, insecticides, nematicides, fungicides, plant growth regulators, acaricides, microorganisms, bactericides and plant activators. Lists of such agricultural chemicals can be found at Alan Wood's website, <www.alanwood.net/pesticides>, and/or in Tomlin, C D S, ed. (2009), and/or *The Pesticide Manual,* 15th Edition, British Crop Protection Counsel, (ISBN: 9781901396188).

The term "pesticide" as used herein is intended to cover compounds active against pests which are intended to repel, kill, or control any species designated a pest including weeds, insects, rodents, fungi, bacteria, or other organisms.

Examples of pesticides include those selected from, for example and not for limitation, insecticides, acaricides, bactericides, fungicides, nematicides and molluscicides.

Suitable additions of fungicidally active ingredients are, for example and not for limitation, representatives of the following classes of active ingredients: strobilurins, triazoles, ortho-cyclopropyl-carboxanilide derivatives, phenylpyrroles, and other systemic fungicides. In one embodiment the crop protection chemical is a strobilurin fungicide such as azoxystrobin, trifloxystrobin, pyraclostrobin, picoxystrobin or fluoxastrobin. In another embodiment the crop protection chemical is a fungicide such as difenoconazole, fludioxonil, thiabendazole, tebuconazole, metalaxyl, mefenoxam, myclobutanil, sedaxane, boscalid, bixafen, or penflufen.

Suitable additions of insecticidally, acaricidally, nematicidally, or molluscicidally active ingredients are, for example and not for limitation, representatives of the following classes of active ingredients: organophosphorus compounds, nitrophenols and derivatives, formamidines, triazine derivatives, nitroenamine derivatives, nitro- and cyanoguanidine derivatives, ureas, benzoylureas, carbamates, pyrethroids, chlorinated hydrocarbons and *Bacillus thuringiensis* products. In one embodiment the crop protection chemical is a neonicitinoid insecticide such as thiamethoxam, clothianidin, imidacloprid or thiacloprid. In another embodiment the crop protection chemical is an insecticide such as abamectin, acetamiprid, thiodicarb, nitenpyram, dinotefuran, fipronil, lufenuron, pyriproxyfen, fluxofenim, chlorantraniliprole, cyantraniliprole, beta-cyfluthrin, lambda-cyhalothrin, fenoxycarb, diafenthiuron, pymetrozine, diazinon, disulphate, profenofos, furathiocarb, cyromazine, cypermethrin, tau-fluvalinate, tefluthrin or *Bacillus thuringiensis* products.

Agricultural chemicals may also include herbicidal safeners. Suitable safeners can be benoxacor, cloquintocet-mexyl, cyometrinil, cyprosulfamide, dichlormid, dicyclonon, dietholate, fenchlorazole-ethyl, fenclorim, flurazole, fluxofenim, furilazole and the corresponding R isomer, isoxadifen-ethyl, jiecaowan, jiecaoxi, mefenpyr-diethyl, mephenate, naphthalic anhydride, oxabetrinil, TI-35, and 2-methoxy-N-[[4-[[(methylamino)carbonyl]amino]phenyl] sulfonyl]-benzamide.

The safeners of the compound of formula I may also be in the form of esters or salts, as mentioned e.g. in The e-Pesticide Manual, version 5.2 (BCPC), 2011. The reference to cloquintocet-mexyl also applies to cloquintocet, and the reference to fenchlorazole-ethyl also applies to fenchlorazole, etc.

Example of microorganisms include those, such as, mycorrhiza, *rhizobia, bacillus* spp., *trichoderma* spp., and *pasteuria* spp.

Suitable bactericides include, but are not limited to, amicarthiazol, bismerthiazol, bronopol, cellocidin, chloramphenicol, copper ammonium carbonate, copper hydroxide, copper octanoate, copper oxychloride, copper oxides, copper sulfate, copper salts of fatty acids, cresol, dichlorophen, dipyrithione, dodicin, ethylicin, fenaminosulf, formaldehyde, hexachlorophene, hydrated lime, hydrargaphen, 8-hydroxyquinoline sulfate, kasugamycin, nitrapyrin, octhilinone, oxolinic acid, oxytetracycline, phenazine oxide, probenazole, saijunmao, saisentong, silver nitrate, streptomycin, tecloftalam, thiodiazole-copper, thiomersal, xinjunan, and zinc thiazole. A particularly preferred bactericide of the present invention is silver nitrate.

The invention claimed is:

1. A method of producing a sugar cane planting unit, the method comprising:
    a. planting a sugar cane propagation material in a first planting container to produce a sugar cane plant, wherein the sugar cane propagation material is a plant produced from tissue culture, or a sugar cane billet, and wherein the first planting container has a volume of 10 to 200 cubic centimeters;
    b. growing the sugar plant in the first planting container to an age of 4 to 18 months, wherein the sugar cane plant has 1 to 4 stalks and at least one stalk has a linear node density of at least 1 node per 3 centimeters of stalk;
    c. harvesting the stalk(s) of the sugar cane plant when the stalk(s) have a length of 10 to 50 centimeters;
    d. cutting the harvested stalk(s) into stalk segments, wherein the stalk segments are cut to a length of 1 to 5 centimeters;
    e. treating the stalk segments with water and a crop protection chemical, wherein the water temperature is 45° C. to 55° C.; and
    f. planting one or more of the treated stalk segments into a second planting container comprising a planting medium to form a planting unit, wherein said second planting container has a volume from 10 to 200 cubic centimeters.

2. The method of claim 1, further comprising transplanting the planting unit into a field.

3. The method of claim 1, wherein the crop protection chemical is a plant growth regulator.

4. The method of claim 3, wherein the plant growth regulator is a plant hormone.

5. The method of claim 4, wherein the plant hormone is selected from cytokinins and auxins.

6. The method of claim 4, wherein the plant hormone is indole-3-butyric acid.

7. The method of claim 3, further comprising treating the stalk segments with a bactericide.

8. The method of claim 7, wherein the bactericide is selected from amicarthiazol, bismerthiazol, bronopol, cellocidin, chloramphenicol, copper ammonium carbonate, copper hydroxide, copper octanoate, copper oxychloride, copper oxides, copper sulfate, copper salts of fatty acids, cresol, dichlorophen, dipyrithione, dodicin, ethylicin, fenaminosulf, formaldehyde, hexachlorophene, hydrated lime, hydrargaphen, 8-hydroxyquinoline sulfate, kasugamycin, nitrapyrin, octhilinone, oxolinic acid, oxytetracycline, phenazine oxide, probenazole, saijunmao, saisentong, silver nitrate, streptomycin, tecloftalam, thiodiazole-copper, thiomersal, xinjunan, and zinc thiazole.

9. The method of claim 8, wherein the bactericide is silver nitrate.

10. The method of claim 1, wherein the water temperature is 48° C. to 53° C.

11. The method of claim 1, wherein treating the stalk segments with water comprises immersing the stalk segments for a soak time of 1 to 10 minutes.

12. The method of claim 11, wherein the water temperature is 48° C. to 53° C.

13. The method of claim 12, wherein the soak time is 2 to 3 minutes.

14. The method of claim 3, wherein the treating the stalk segments with the plant growth regulator comprises immersing the stalk segment in a plant growth regulator solution having a plant growth regulator concentration of 0.01 to 100 g/L.

15. The method of claim 14, wherein the plant growth regulator is indole-3-butyric acid and the indole-3-butyric acid concentration is 0.5 to 10 g/L.

16. The method of claim 9, wherein the treating the stalk segments with silver nitrate comprises immersing the stalk segment in a silver nitrate solution having a silver nitrate concentration of 0.01 to 10 g/L.

17. The method of claim 1, wherein the crop protection chemical is a fungicide or insecticide.

18. The method of claim 1, wherein the planting the one or more stalk segments comprises planting a single stalk segment into the second planting container.

19. The method of claim 1, wherein the sugar cane propagation material is a sugar cane billet; and wherein the sugar cane billet consists of a single node.

20. A method of producing a sugar cane planting unit, the method comprising:
  a. planting one or more stalk segments into a second planting container comprising a planting medium to form a planting unit, wherein said second planting container has a volume from 10 to 200 cubic centimeters, and wherein the one or more stalk segments was produced by the steps comprising:
    i. planting a sugar cane propagation material in a first planting container to produce a sugar cane plant, wherein the sugar cane propagation material is a plant produced from tissue culture, or a sugar cane billet, and wherein the first planting container has a volume of 10 to 200 cubic centimeters;
    ii. growing the sugar plant in the first planting container to an age of 4 to 18 months, wherein the sugar cane plant has 1 to 4 stalks and at least one stalk has a linear node density of at least 1 node per 3 centimeters of stalk;
    iii. harvesting the stalk(s) of the sugar cane plant when the stalk(s) have a length of 10 to 50 centimeters;
    iv. cutting the harvested stalk(s) into stalk segments, wherein the stalk segments are cut to a length of 1 to 5 centimeters; and
    v. treating the stalk segments with water and a crop protection chemical.

* * * * *

UNITED STATES PATENT AND TRADEMARK OFFICE
CERTIFICATE OF CORRECTION

| | |
|---|---|
| PATENT NO. | : 11,612,121 B2 |
| APPLICATION NO. | : 16/093955 |
| DATED | : March 28, 2023 |
| INVENTOR(S) | : Silva et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 885 days.

Signed and Sealed this
Thirty-first Day of December, 2024

Derrick Brent
*Acting Director of the United States Patent and Trademark Office*